(12) United States Patent
Vogt

(10) Patent No.: US 10,143,773 B2
(45) Date of Patent: Dec. 4, 2018

(54) MALLEABLE, BIODEGRADABLE HEMOSTATIC AGENT

(71) Applicant: Heraeus Medical GmbH, Wehrheim (DE)

(72) Inventor: Sebastian Vogt, Erfurt (DE)

(73) Assignee: Heraeus Medical GmbH, Wehrheim (DE)

( * ) Notice: Subject to any disclaimer, the term of this patent is extended or adjusted under 35 U.S.C. 154(b) by 0 days.

(21) Appl. No.: 14/885,049

(22) Filed: Oct. 16, 2015

(65) Prior Publication Data

US 2016/0038630 A1 Feb. 11, 2016

Related U.S. Application Data

(62) Division of application No. 13/438,371, filed on Apr. 3, 2012, now abandoned.

(30) Foreign Application Priority Data

Apr. 6, 2011 (DE) ........................ 10 2011 016 277

(51) Int. Cl.
*A61L 24/00* (2006.01)
*A61L 27/28* (2006.01)
*A61L 24/04* (2006.01)

(52) U.S. Cl.
CPC ....... *A61L 24/0042* (2013.01); *A61L 24/0015* (2013.01); *A61L 24/046* (2013.01); *A61L 27/28* (2013.01); *A61L 2300/404* (2013.01); *A61L 2300/406* (2013.01); *A61L 2300/418* (2013.01); *A61L 2300/45* (2013.01); *A61L 2300/606* (2013.01); *A61L 2400/04* (2013.01); *A61L 2430/02* (2013.01)

(58) Field of Classification Search
CPC ................................................ A61L 2300/418
See application file for complete search history.

(56) References Cited

U.S. PATENT DOCUMENTS

| 4,192,021 | A | | 3/1980 | Deibig et al. |
|---|---|---|---|---|
| 4,595,713 | A | | 6/1986 | St. John |
| RE32,208 | E | * | 7/1986 | Mattei et al. |
| 5,681,873 | A | | 10/1997 | Norton et al. |
| 7,923,019 | B2 | | 4/2011 | Kuhn et al. |
| 8,092,824 | B2 | | 1/2012 | Kuhn et al. |
| 8,105,628 | B2 | | 1/2012 | Kronenthal |
| 8,309,131 | B2 | | 11/2012 | Kronenthal |
| 2006/0002976 | A1 | | 1/2006 | Kronenthal |
| 2006/0127437 | A1 | | 6/2006 | Kennedy et al. |
| 2006/0127444 | A1 | | 6/2006 | Kuhn et al. |
| 2008/0145392 | A1 | | 6/2008 | Knaack et al. |
| 2009/0286886 | A1 | | 11/2009 | Fisher et al. |
| 2011/0002974 | A1 | | 1/2011 | Wellisz et al. |
| 2012/0258159 | A1 | | 10/2012 | Vogt |

FOREIGN PATENT DOCUMENTS

| DE | 1985889 U | 5/1968 |
|---|---|---|
| DE | 3229540 A1 | 2/1984 |
| DE | 102004060666 B3 | 3/2006 |
| DE | 102005002703 A1 | 7/2006 |
| EP | 0109310 A2 | 5/1984 |
| EP | 1142597 A1 | 10/2001 |
| JP | S59-101155 A | 6/1984 |
| JP | H07-118157 A | 5/1995 |
| JP | 2006-167469 A | 6/2006 |
| JP | 2006-521425 A | 9/2006 |
| JP | 2007-506505 A | 3/2007 |
| JP | 2007-515196 A | 6/2007 |
| JP | 2008-523149 A | 7/2008 |
| WO | 2004006890 A1 | 1/2004 |

OTHER PUBLICATIONS

Dibilidox-Alvarado, JAOCS, 74/2, 1997, 69-76.*
Office Action dated Oct. 25, 2011 in DE Application No. 10 2011 016 277.1.
Office Action dated May 27, 2013 in AU Application No. 2012201598.
English translation of an Office Action dated Nov. 19, 2013 in JP Application No. 2012-068946.
Office Action dated Dec. 30, 2013 in CA Application No. 2,771,531.
Extended European Search Report dated Sep. 26, 2014 in EP Application No. 12001660.5.
Office Action dated Jul. 30, 2013 in U.S. Appl. No. 13/438,371 by Vogt.
Office Action dated May 20, 2014 in U.S. Appl. No. 13/438,371 by Vogt.
Office Action dated Apr. 17, 2015 in U.S. Appl. No. 13/438,371 by Vogt.

* cited by examiner

*Primary Examiner* — Kyle A Purdy
(74) *Attorney, Agent, or Firm* — Panitch Schwarze Belisario & Nadel LLP

(57) ABSTRACT

A malleable, biodegradable hemostatic agent is provided that can be used for mechanical sealing of bleeding bone tissue, as well as a method for forming a malleable, biodegradable hemostatic agent of this type, and a medical implant having a coating that includes a malleable, biodegradable hemostatic agent of this type. The malleable, biodegradable hemostatic agent contains (a) at least one saturated glycerol-1,2,3-tri-fatty acid ester having a melting temperature above 37° C., (b) at least one filling agent present in particulate form, at least in part, and having a melting temperature above 37° C., and (c) at least one compound having a melting temperature not above 37° C. and a solubility at a temperature of 25° C. of less than 50 grams per liter of water.

17 Claims, No Drawings

MALLEABLE, BIODEGRADABLE HEMOSTATIC AGENT

CROSS-REFERENCE TO RELATED APPLICATION

This application is a division of U.S. patent application Ser. No. 13/438,371, filed Apr. 3, 2012, the disclosure of which is hereby incorporated by reference in its entirety.

BACKGROUND OF THE INVENTION

The invention relates to a malleable, biodegradable hemostatic agent that can be used for mechanical sealing of bleeding bone tissue, a method for forming a malleable, biodegradable hemostatic agent of this type, and a medical implant having a coating that comprises a malleable, biodegradable hemostatic agent of this type.

Hemostasis is attained during surgeries by different procedures depending on the anatomical situation, e.g. electrocoagulation (cauterization) of the blood vessels. In a number of surgeries in the region of the skull and, predominantly, at the sternum, bone wax is used to seal the capillary vessels and thus to achieve hemostasis, because of the strong bleeding that occurs in these locations due to the anatomical situation. In the process, the bone wax is first kneaded to be soft by the surgeon and then pressed directly onto and/or into the bleeding bone areas. This blocks the flow of blood, which causes hematomas to arise and the supply vessels to ultimately become closed by fibrin.

Bone wax has been known since the 19th century and generally contains bleached bees wax and a plasticizer. Substances including almond oil, Vaseline, palmitic acid, isopropyl ester, and myristic acid isopropyl ester, can be used as plasticizer. Conventional bone waxes are viscous masses and relatively difficult to knead at room temperature. The plasticizer contained in the bees wax serves to soften the wax and make it malleable while the bone wax is being kneaded owing to the warmth of the hand. Bone waxes based on bees wax are considered to be non-degradable in the human body. Frequent components of bees wax include esters of myristic acid and higher alcohols, e.g. myristic acid myricyl ester. Presumably, the human body has no suitable enzymes for degradation of the very hydrophobic esters in a reasonable amount of time. The bone waxes that are currently commercially available have a very good hemostatic effect, but lead not infrequently to damage in the human body. See: S. E. Katz, J. Rotmann, "Adverse effects of bone wax in surgery of the orbit," *Ophthal. Plast. Reconstr.*, 12(2):121-126 (1996); M. Lavigne et al., "Bone-wax granuloma after femoral neck osteoplasty," *Can. J. Surg.*, 51(3): E58-60 (2008); R. T. Allison, "Foreign body reactions and an associated histological artifact due to bone wax," *Br. J. Biomed. Sci.*, 51(1):14-17 (1994); O. Eser et al., "Bone wax as a cause of foreign body reaction after lumbar disc surgery: A case report" *Adv. Ther.*, 24(3):594-7 (2007). The very good adhesive effect on moist and also fatty bone tissue can be seen as the main advantage of conventional bone waxes.

A number of alternatives to conventional bone wax are known according to the prior art. European Patent Application Publication EP 0 109 310 A2, for example, discloses a wax-like mass that is based on calcium salts of fatty acids and oligomers of hydroxycarbonic acids.

From U.S. Pat. No. 4,595,713, German published patent application DE 32 29 540 A1, DE Utility Model 1 985 889, and European Patent Application Publication EP 1 142 597 A1 are known wax-like compositions that contain oligoesters of hydroxycarbonic acids, for example lactic acid and 6-hydroxycarbonic acid. It has been evident that acidic degradation products, which adversely affect the bone tissue due to local lowering of the pH value, are generated during hydrolytic degradation upon use of these wax-like compositions.

Compositions based on polyethers are a promising development (see U.S. Patent Application Publication Nos. US 2009/0286886 and US 2011/0002974). For example, polypropylene glycol-co-ethylene glycols) can be used as polyethers. These compositions are kneadable and spreadable when exposed to the warmth of a hand. However, the good solubility of the polyethers in aqueous media must be seen as a disadvantage. This leads to adhesion of the compositions being more difficult in the presence of strongly bleeding bone tissue due to beginning dissolution of the wax-like composition. This may possibly lead to secondary bleeding which in turn causes the seal to begin to be dissolved or be fully dissolved. However, it is a particular advantage of the mixtures that they possess no barrier function for bone healing whatsoever and are completely eliminated through the renal pathway, see A. Suwan et al., "Controversial role of two different local hemostatic agents on bone healing," *J. Am. Sci.*, 6(12):15-163 (2010).

Accordingly, there still is a need for a malleable, biodegradable hemostatic agent that is not associated with the disadvantages described above. The hemostatic agent should be a mass, which is kneadable and malleable at body temperature, similar to the bone wax that is commercially available thus far. The viscosity of the hemostatic agent should be high enough for the mass to withstand the pressure of bleeding. Furthermore, the hemostatic agent should have sufficient cohesion, such that it does not disintegrate or dissolve within few minutes upon contact with blood or other aqueous media. Moreover, the hemostatic agent should not release any substantial quantities of acidic or alkaline components, in order to not damage the bone tissue by a non-physiological pH. Moreover, the material should be biodegradable or it should be subject to renal elimination, such that there is no permanent barrier effect of the material that might impair the healing process of the bone tissue. In addition, the mass should not stick to rubber gloves when it is being kneaded or applied.

BRIEF SUMMARY OF THE INVENTION

Therefore, according to the invention, an object is to provide an advantageous malleable, biodegradable hemostatic agent that can be used for mechanical sealing of bleeding bone tissue. Another object according to the invention is to provide a method for forming a malleable, biodegradable hemostatic agent of this type. Another object of the invention is to provide a medical implant having a coating that comprises a malleable, biodegradable hemostatic agent of this type.

Accordingly, the invention provides a malleable, biodegradable hemostatic agent that comprises (a) at least one saturated glycerol-1,2,3-tri-fatty acid ester having a melting temperature above 37° C., (b) at least one filling agent present in particulate form, at least in part, and having a melting temperature above 37° C., and (c) at least one compound having a melting temperature not above 37° C. and a solubility at a temperature of 25° C. of less than 50 grams per liter of water.

The invention also provides a method for forming a malleable, biodegradable hemostatic agent of this type, comprising the steps: (a) providing a malleable, biodegradable hemostatic agent according to the above description, (b) heating the malleable, biodegradable hemostatic agent to a temperature in the range of 35-40° C., and (c) forming the heated malleable, biodegradable hemostatic agent.

Moreover, the invention provides a medical implant having a coating that comprises a malleable, biodegradable hemostatic agent of this type.

The invention is based on the surprising finding that interaction of components (a), (b), and (c) allows a mixture to be provided that acts effectively as a hemostatic agent and can be used to seal bleeding bone tissue. It is particularly surprising in this context that the hemostatic agent according to the invention based on components (a) by (c) is present as a wax-like, kneadable mass that adheres both to dry and wet surfaces. The viscosity and mechanical stability of the mixture are surprisingly sufficiently high to allow it to be used to arrest bleeding as an effective hemostatic agent and to withstand the bleeding pressures that occur in the case of injury. Although the mixture is biodegradable, it surprisingly has sufficient mechanical stability not to disintegrate upon contact with blood.

Without wishing to be limited by theoretical considerations, the advantageous properties appear to be based on the formation of a stable matrix in which the filling agents, which are present in particulate form, are bonded to each other by the at least one saturated glycerol-1,2,3-tri-fatty acid ester having a melting temperature above 37° C. The additional use of at least one compound having a melting temperature not above 37° C. and a solubility at a temperature of 25° C. of less than 50 grams per liter of water ensures that the mixture formed as such is malleable. Surprisingly, this does not impair the mechanical stability of the hemostatic agent thus generated. In this context, it is particularly surprising that the compound having a melting temperature not above 37° C. and a solubility at a temperature of 25° C. of less than 50 grams per liter of water, does not exit or is not released from the hemostatic agent, but rather remains firmly enclosed in the system that presumably is based on the formation of a matrix.

DETAILED DESCRIPTION OF THE INVENTION

According to the invention, a hemostatic agent is provided. According to the invention, a hemostatic agent shall be understood to be compositions having hemostatic properties.

The hemostatic agent according to the invention is malleable or plastically workable. Herein, malleability shall be understood to be the property of the hemostatic agent to change shape irreversibly when exposed to a force and to maintain the shape after being exposed to a force.

Furthermore, the hemostatic agent according to the invention is biodegradable. Herein, substances shall be called biodegradable if they can be degraded by the human body.

The hemostatic agent of the present invention preferably has a pH in water in the range of 5.0 to 9.0, more preferably a pH in the range of 5.5 to 8.5, even more preferably a pH in the range of 6.0 to 8.0, and particularly preferably a pH in the range of 6.5 to 7.5, at room temperature of 25° C.

According to a preferred embodiment, the hemostatic agent according to the invention contains no oligoesters of hydroxycarbonic acids and in particular no oligoesters of lactic acid or 6-hydroxycaproic acid.

The biodegradable hemostatic agent according to the invention contains, as component (a), at least one saturated glycerol-1,2,3-tri-fatty acid ester having a melting temperature above 37° C. According to general usage, saturated glycerol-1,2,3-tri-fatty acid ester shall be understood to be a glycerol ester having three fatty acid residues which each have no carbon-carbon multiple bonds.

The melting temperature of the at least one saturated glycerol-1,2,3-tri-fatty acid ester used as component (a) is above 37° C., preferably above 40° C., more preferably above 42° C., and even more preferably above 45° C.

In the scope of the entire present invention, melting temperature shall be understood to be the temperature at which the respective substance transitions from the solid to the liquid state of aggregation. If the transition of a substance from the solid to the liquid state of aggregation does not occur at a certain temperature, but rather in a melting range, the scope of the invention has the melting temperature understood to be the lower of the two limit temperatures of the melting range.

A melting temperature being in the specified range ensures that the saturated glycerol-1,2,3-tri-fatty acid ester does not melt and the hemostatic agent is not softened at body temperature of 37° C.

The at least one component (a) is preferably selected from the group consisting of saturated glycerol-1,2,3-tri-fatty acid esters that comprise at least one fatty acid residue of 12-28 carbon atoms, more preferably of 14-24 carbon atoms, and even more preferably of 12-22 carbon atoms. According to a particularly preferred embodiment, component (a) is preferably selected from the group consisting of saturated glycerol-1,2,3-tri-fatty acid esters that have three fatty acid residues of 12-28 carbon atoms, preferably of 14-24 carbon atoms, and even more preferably of 12-22 carbon atoms. The fatty acid residues can be branched, but are preferably non-branched. Moreover, the fatty acid residues can be substituted, optionally. However, the fatty acid residues preferably are non-substituted. The fatty acid residues are preferably selected from the group consisting of fatty acid residues of lauric acid, myristic acid, palmitic acid, margaric acid, stearic acid, arachic acid, and behenic acid.

The esters used as component (a) can have identical residues. On the other hand, component (a) can just as well be a mixed ester. Herein, mixed esters shall be understood to be esters that comprise at least two different fatty acid residues. In particular, three different fatty acid residues can be present in the mixed esters.

According to a preferred embodiment, component (a) is selected from the group consisting of glycerol-1,2,3-behenic acid ester, glycerol-1,2,3-tristearic acid ester, and glycerol-1,2,3-tripalmitic acid ester.

Component (a) appears to work as a matrix forming substance in the hemostatic agent according to the invention. In this context, it appears to assume the role of a binding agent that provides for extraordinarily high mechanical stability of the hemostatic agent through strong cohesion to the remaining components, in particular to the filling agent that is present as component (b).

The at least one component (b) is at least one filling agent, which is at least in partly present in particulate form and has a melting temperature above 37° C. The melting temperature of the filling agent used as component (b) preferably is above 40° C., more preferably is above 42° C., and even more preferably is above 45° C. This ensures that the filling agent does not melt and that the hemostatic agent is not softened at body temperature of 37° C.

Preferably, the filling agent used as component (b) is hydrophilic. According to a preferred embodiment, the filling agent has a solubility at a temperature of 25° C. of at last 70 grams per liter of water, more preferably a solubility of at least 100 grams per liter of water, and even more preferably a solubility of at least 130 grams per liter of water.

The filling agent is at least in partly present in particulate form. Preferably at least 30 percent, more preferably at least 50 percent, even more preferably at least 70 percent, particularly preferably at least 90 percent, even more particularly preferably at least 95 percent, and in particular at least 99 percent of the filling agent are present in particulate form.

The particles of the filling agent that are present may differ in shape. For example, the particles of the filling agent can be spherical, cubic or irregular in shape. The particles of the filling agent preferably have a mean particle diameter in the range of 50 nm to 500 µm, more preferably in the range of 100 nm to 100 µm, and even more preferably in the range of 500 nm to 100 µm. Herein, the mean particle diameter shall be understood to mean that at least 50% of the particles have the specified particle diameter.

According to a preferred embodiment, component (b) is a hydrophilic filling agent. Filling agents with a pH value in the range of 6-8 in the presence of water have proven to be particularly advantageous.

Component (b) is preferably selected from the group consisting of polyethers and calcium compounds.

According to an embodiment of the invention, the polyether that is suitable as component (b) is selected from the group consisting of polymers of at least ethylene oxide, polymers of at least propylene oxide, copolymers of at least ethylene oxide, copolymers of at least propylene oxide, and copolymers of at least ethylene oxide and propylene oxide. The copolymers of ethylene oxide and propylene oxide can just as well be block copolymers, in particular poloxamers.

In this context, the use of polyalkylethers, for example poloxamers, polyethylene glycols or poly(propylene glycol-co-ethylene glycol) has proven to be particularly advantageous.

According to another preferred embodiment, the polyether used as component (b) is selected from the group consisting of polyethylene glycol 35,000, polyethylene oxide 100,000, polyethylene oxide 300,000, polyethylene oxide 1,000,000, and polypropylene glycol-co-ethylene glycol) having a polyoxyethylene content in the range of 50-80% by weight.

Moreover, it can be preferred to use a hydrophilic filling agent having a softening temperature above 45° C. as component (b). It has been evident that hydrophilic filling agents having a softening point of 45° C. cause the hemostatic agent according to the invention to show surprisingly high mechanical stability.

According to another preferred embodiment, component (b) can be a calcium compound. The calcium compound can be, for example, a calcium salt.

According to the invention, a calcium salt shall be understood to mean a salt that contains at least calcium ions as the cationic component. Further cationic components can be present in the salt aside from the calcium ions. The further cationic components can be, for example, cations of elements of the first or second main group of the Periodic Table of elements, in particular of sodium, magnesium or strontium.

It has proven to be particularly advantageous that the calcium compound used as component (b) is the salt of at least one inorganic acid. The calcium compound may also contain further anionic components aside from anions derived from an inorganic acid. The further anionic components can be, for example, halogenide anions or hydroxide anions. Preferably, the salt of at least one inorganic acid is selected from the group consisting of calcium salts of carbonic acid, phosphoric acids, and sulphuric acid. Accordingly, the calcium salt can be, for example, calcium carbonate, dolomite, α-tricalcium carbonate, β-tricalcium carbonate, hydroxylapatite, carbonate apatite, octacalciumphosphate, calcium phosphate made amorphous, β-tricalcium sulfate, calcium sulfate dihydrate, and calcium sulfate hemihydrate. The calcium salts are very biocompatible and are degraded by the action of osteoclasts or also by simple dissolution.

The use of calcium sulfate hemihydrate has proven to be particularly advantageous. A hemostatic agent according to the invention that contains calcium sulfate hemihydrate as component (b) can surprisingly harden independently by the action of water or aqueous liquids, such as blood, without the extraordinarily high viscosity and mechanical stability of the hemostatic agent being lost.

It has been evident that component (b) ensures strong cohesion to the remaining components in the hemostatic agent according to the invention, in particular to the saturated glycerol-1,2,3-tri-fatty acid ester having a melting temperature above 37° C. used as component (a). Surprisingly, component (b) appears to act also as volumizer. Accordingly, it has been evident that component (b) can become dissolved from the hemostatic agent according to the invention after prolonged exposure to water or aqueous liquids, for example blood, though without the mechanical stability of the hemostatic agent being impaired. Surprisingly, the dissolution creates hollow spaces and then a pore system in the hemostatic agent, which allows, for example, bone tissue to penetrate into the hemostatic agent thus allowing the healing process to be accelerated substantially as compared to hemostatic agents with a barrier effect.

The hemostatic agent of the present invention contains as component (c) at least one compound having a melting temperature not above 37° C. and a solubility at a temperature of 25° C. of less than 50 grams per liter of water.

According to a preferred embodiment, the compound contained in the hemostatic agent as component (c) has a melting temperature not above 36° C., more preferably a melting temperature not above 35° C., even more preferably a melting temperature not above 34° C., particularly preferably a melting temperature not above 32° C., and even more particularly preferably a melting temperature not above 30° C.

According to another preferred embodiment, the solubility of component (c) at a temperature of 25° C. is less than 40 grams per liter of water, more preferably is less than 30 grams per liter of water, even more preferably is less than 25 grams per liter of water, particularly preferably is less than 15 grams per liter of water, even more particularly preferably is less than 10 grams per liter of water, and in particular is less than 5 grams per liter of water.

Component (c) can be, for example, a saturated fatty acid ester. According to general usage, a saturated fatty acid ester is understood to be an ester compound having one or more fatty acid residues, wherein the fatty acid residues each are free of carbon-carbon multiple bonds.

The fatty acid residues of the saturated fatty acid esters used as component (c) preferably have 8-28 carbon atoms, more preferably 8-22 carbon atoms, and even more preferably 8-18 carbon atoms. The fatty acid residues can be branched, but preferably are non-branched. Moreover, the fatty acid residues can have substituents, but preferably are non-substituted. Conceivable fatty acid residues are, for example, caprylic acid residues, pelargonic acid residues, capric acid residues, lauric acid residues, myristic acid residues, palmitic acid residues, margaric acid residues, stearic acid residues, arachic acid residues, and behenic acid residues.

According to a preferred embodiment, the saturated fatty acid ester is selected from the group consisting of (i) esters of polyols and at least one fatty acid, (ii) alkyl fatty acid esters, and (iii) esters of polyethers and fatty acids.

According to an embodiment of the invention, the saturated fatty acid ester is an ester of a polyol and at least one fatty acid. This can be, for example, the ester of a polyol having a chain length of 2-4 carbon atoms and preferably the ester of a polyol having a chain length of 3 carbon atoms. The polyol can be substituted or non-substituted. Esters of glycerol, 1,2-propanediol, and 1,3-propanediol have proven to be particularly preferred. Preferred esters of polyols and at least one fatty acid are selected from the group consisting of glycerol monoesters, glycerol diesters, glycerol triesters, 1,2-propanediol monoesters, 1,2-propanediol diesters, 1,3-propanediol monoesters, and 1,3-propanediol diesters. The fatty acid residues of the esters of polyols and at least one fatty acid can be identical. However, the esters can just as well be mixed esters of polyols and more than one fatty acid. Examples of esters of polyols and at least one fatty acid to be mentioned include glycerol-1,2,3-trioctylester, mixed esters of glycerol and caprylic acid and lauric acid, propane-1,2-diol-difatty acid esters, and fatty acid esters of 1,3-dihydroxy-2,2-di(hydroxymethyl)propane.

According to an alternative embodiment, the saturated fatty acid ester can just as well be an alkyl fatty acid ester. The alkyl residue of the alkyl fatty acid esters preferably has a chain length of 1-8 carbon atoms, more preferably a chain length of 1-6 carbon atoms, even more preferably a chain length of 1-4 carbon atoms, and particularly preferably a chain length of 1-3 carbon atoms. The alkyl residue of the alkyl fatty acid esters can be branched or non-branched. Moreover, the alkyl residue of the alkyl fatty acid esters can be substituted, optionally. Preferably, the alkyl fatty acid ester is selected from the group consisting of methyl fatty acid esters, ethyl fatty acid esters, propyl fatty acid esters, and isopropyl fatty acid esters. Preferably, the alkyl fatty acid esters are selected from the group consisting of lauric acid ethylester, myristic acid methylester, myristic acid ethylester, myristic acid isopropylester, palmitic acid methylester, palmitic acid ethylester, and palmitic acid isopropylester.

According to another alternative embodiment, the saturated fatty acid ester used as component (c) is the ester of a polyether and a fatty acid. Preferably, the ester is selected from the group consisting of esters of fatty acids and polymers of at least ethylene oxide, esters of fatty acids and polymers of at least propylene oxide, esters of fatty acids and copolymers of at least ethylene oxide, and esters of fatty acids and copolymers of at least propylene oxide. It has proven to be particularly advantageous that the esters of polyethers and fatty acids used as component (c) are selected from the group consisting of ethylene glycol fatty acid esters.

The presence of component (c) in the hemostatic agent according to the invention lowers the melting range and thus ensures the malleability of the hemostatic agent. Moreover, component (c) also acts as a lubricant in that it clearly lowers the friction due to the remaining components. Moreover, it has surprisingly been evident that component (c) is capable of reducing the otherwise inevitable recrystallization of the glycerol-1,2,3-tri-fatty acid ester used as component (a) in the hemostatic agent.

The composition of the hemostatic agent according to the invention with regard to components (a), (b), and (c) is not particularly limited.

According to a preferred embodiment of the invention, the hemostatic agent contains 3-50% by weight of the at least one component (a), 10-80% by weight of the at least one component (b), and 10-50% by weight of the at least one component (c), relative to the total weight of the hemostatic agent. According to a particularly preferred embodiment, the hemostatic agent of the present invention contains 5-40% by weight of the at least one component (a), 20-75% by weight of the at least one component (b), and 20-40% by weight of the at least one component (c), relative to the total weight of the hemostatic agent.

It has proven to be particularly advantageous for the formation of a stable matrix that the solubility of component (b) in component (c) be low. Accordingly, the solubility of component (b) at a temperature of 25° C. preferably is less than 50 grams per liter of component (c), more preferably is less than 20 grams per liter of component (c), even more preferably is less than 10 grams per liter of component (c), particularly preferably is less than 5 grams per liter of component (c), and even more particularly preferably is less than 3 grams per liter of component (c).

Moreover, for formation of a stable matrix, it has been found to be particularly advantageous that the solubility of component (b) in components (a) and (c) of the hemostatic agent be low. Accordingly, the solubility at a temperature of 25° C. of the at least one component (b) preferably is less than 5% by weight, more preferably is less than 3% by weight, and even more preferably is less than 1% by weight, relative to the total weight of components (a) and (c).

The hemostatic agent according to the invention can optionally comprise further components aside from components (a), (b), and (c).

For example, at least one other calcium salt can be contained in the hemostatic agent according to the invention. Preferably, the calcium salt is selected from the group consisting of calcium chloride, calcium acetate, and calcium lactate. It has been evident that the calcium ions contained in the calcium salts act on secondary blood coagulation as blood coagulation factor IV and thus promote blood coagulation. Preferably, the fraction of the further calcium salt is less than 2% by weight, relative to the total weight of the hemostatic agent. Adding at least one easily soluble calcium salt selected from the group consisting of calcium chloride, calcium acetate, and calcium lactate or the at least one fibrinolysis inhibitor allows the hemostatic agent according to the invention to not only mechanical hemostasis, but also hemostasis by a biochemical route.

According to another preferred embodiment, the hemostatic agent according to the invention further contains at least one fibrinolysis inhibitor. Conceivable fibrinolysis inhibitors are, in particular, members of the group of ε-aminocarbonic acids. ε-Aminocarbonic acids are lysine analogues and act on plasminogen, a precursor of plasmin, in order to inhibit the formation of plasmin, which normally effects enzymatic cleavage of fibrin. As a result, this leads to stabilization of fibrin, which promotes blood coagulation locally. The ε-aminocarbonic acids, 6-aminocaproic acid, 4-(aminomethyl)benzoic acid, and trans-4-(aminomethyl)cyclohexan-1-carbonic acid have proven to be particularly advantageous for this purpose.

According to a further preferred embodiment, the hemostatic agent according to the invention contains at least one substance selected from the group consisting of antibiotics and antiseptic agents. Members of the groups of aminoglycoside antibiotics, glycopeptide antibiotics, lincosamide antibiotics, and peptide antibiotics are preferred as antibiotics. Conceivable antiseptic agents are, for example, polyhexanide, octenidine hydrochloride, and chlorhexidine. The presence of the antibiotics and/or antiseptic agents allows effective local infection protection to be attained by means of the hemostatic agent.

The hemostatic agent according to the invention can be manufactured by a variety of routes.

According to an embodiment of the invention, the hemostatic agent is manufactured by first placing all components of the hemostatic agent in a suitable mixing vessel. Subsequently, the individual components can be mixed, for example by stirring.

Preferably, the mixture thus obtained is then heated. It has proven to be advantageous to heat the mixture to a temperature above the melting point of components (a), (b), and (c). For example, the mixture can be heated to a temperature above 50° C., preferably to a temperature above 60° C., and even more preferably to a temperature above 70° C. In the process, the mixture can be heated, for example, to a temperature in the range of 50° C.-100° C., preferably to a temperature in the range of 60° C.-95° C., and even more preferably to a temperature in the range of 70° C.-90° C. It can therefore be advantageous according to the invention that a melted mass be formed during the heating of the mixture.

Preferably, the heating can proceed for a period of time of at least 5 minutes. For example, the mixture can be heated for a period of time of 5 minutes-4 hours, preferably for a period of time of 15 minutes-2 hours, and even more preferably for a period of time of 30 minutes-60 minutes. It is preferable for the mixture to be stirred in this context. Stirring the melted mass allows simple homogenization of the mixture to be attained and the formation of a matrix by components (a), (b), and (c) to be simplified.

Subsequently, the heated mixture can be cooled down. Preferably, the mixture is cooled down to a temperature in the range of 15° C.-30° C., and more preferably to a temperature in the range of 20° C.-25° C.

Subsequently, the cooled mixture can be further homogenized, if required. Homogenization can be carried out, for example, by means of kneading or triturating the mixture.

Components other than components (a), (b), and (c) can be added to the mixture prior to components (a), (b) or (c), concurrently with components (a), (b), and (c) or separate from these in one or more of the further procedural steps.

According to an alternative embodiment of the invention, only one or two, but not all, of components (a), (b), and (c) are placed in a suitable mixing vessel. Usually, it is not critical which of the components is placed in the mixing vessel first. If one component is to be placed in the mixing vessel first, the component preferably is component (a) or component (c). If two of the components are placed in the mixing vessel, the components preferably are components (a) and (c). The remaining component or remaining components not placed in the mixing vessel initially can be added at a later point in time. The addition of the component(s) can proceed, for example, after heating or cooling down of the component(s) already placed in the mixing vessel.

The hemostatic agent of the present invention described herein is structured such that it is malleable and easily kneadable and strongly adheres to dry and wet surfaces at a temperature of 37° C. Therefore, the invention also relates to a method for forming the hemostatic agent according to the invention.

In this method, the hemostatic agent described above is initially provided. The form, in which it is provided, is not limited. However, usually the hemostatic agent is provided in a container. The container is preferably structured such that it can be opened easily by a user. Conceivable suitable containers are, for example, tins, bottles, bags or cartridges, each of which can be provided with suitable closures. The hemostatic agent is usually removed from the bag by the user after opening the container.

After it has been provided, the hemostatic agent is heated. Heating preferably is carried out to a temperature in the range of 35-40° C. The hemostatic agent is easy to shape at this temperature.

According to a preferred embodiment, the heating is effected by at least one of the user's hands. The heating of the hemostatic agent according to the invention by the user can proceed, for example, by means of kneading the hemostatic agent. Since the hemostatic agent of the present invention does not adhere to the gloves of the user, the user can wear gloves while heating the hemostatic agent with at least one of the user's hands. However, in this context, the gloves should preferably be selected in such a manner that the warmth of the hand of the user can be transmitted via the glove to the hemostatic agent. Gloves made of materials with correspondingly suitable thermal conductivity are well-known according to the prior art and are usually sold as gloves suitable for laboratory activities or medical activities.

According to an alternative embodiment, it is feasible just as well to heat the hemostatic agent by other means, preferably by the addition of external heat, for example by irradiating it. Accordingly, the heating is not effected by one of the user's hands according to this embodiment. However, heating by at least one of the user's hands has proven to be particularly preferred.

Moreover, the hemostatic agent of the present invention is formed. Preferably, forming is understood to be any change of the shape or geometry of the hemostatic agent provided.

The forming is preferably effected by at least one of the user's hands. The forming can also be carried out while the user wears gloves. Forming of the hemostatic agent according to the invention can already lead to heating of the hemostatic agent, for example by kneading of the hemostatic agent by a user. Accordingly, the scope of the invention includes the step of heating the hemostatic agent and the step of forming the hemostatic agent are effected by a continuous action of the user. Moreover or instead, the forming can be effected after heating the hemostatic agent to a temperature in the range of 35-40° C. The forming can serve, for example, to give the hemostatic agent a shape that is suitable for mechanical sealing of bleeding bone tissue during a subsequent surgery. After forming, the hemostatic agent can be used instantaneously by the user in a surgery.

The hemostatic agent of the present invention can be used for different medical purposes.

According to an embodiment, the hemostatic agent is used for mechanical closure of bleeding bone wounds. For this purpose, the hemostatic agent serves as a bone sealing agent. It can be pressed onto or into bleeding bone areas by the user for this purpose.

Moreover, it is also feasible to use the hemostatic agent of the invention as bone replacement material. It can be of advantage in this process, in particular, to replace parts of damaged bones with the hemostatic agent according to the invention.

The invention also relates to a medical implant having a coating comprising the hemostatic agent according to the invention. The hemostatic agent according to the invention can therefore be used for the coating of medical implants. In this context, medical implants shall be understood to mean materials and devices that are inserted into the body, at least in part, in the course of a surgical intervention.

The medical implants can be manufactured, for example, from metal or plastic material. The medical implants preferably are articular endoprostheses, osteosynthesis materials, vascular prostheses, or hernial meshes. Conceivable articular endoprostheses are, e.g., knee endoprostheses and hip endoprostheses. For example, plates, marrow nails, and screws can serve as osteosynthesis materials.

According to the invention, a coating of a medical implant shall be understood to mean a layer that covers and adheres to at least a part of a surface of the medical implant. The coating of the medical implant comprises the hemostatic agent according to the invention. Accordingly, the invention can provide the coating to be formed fully by the hemostatic agent according to the invention or optionally that the coating contains further components.

For coating, it is preferable to apply the hemostatic agent of the present invention, which has been heated and formed appropriately, to at least one surface of the medical implant, at least in part. The application can be carried out, for example, in that at least a part of the heated and formed hemostatic agent is pressed onto the at least one surface of the medical implant, or at least part of the hemostatic agent is applied by a relative motion of the hemostatic agent with respect to the medical implant surface to be coated, during which the hemostatic agent contacts the medical implant surface to be coated (for example by spreading it).

EXAMPLES

The invention is illustrated by the following examples, though these may not be construed such as to limit the invention in any way or form.

The following chemicals were used in the examples described below:
Glycerol-1,2,3-tristearate;
Glycerol-1,2,3-tripalmitate;
Glycerol-1,2,3-trimyristate,
Glycerol-1,2,3-tristearate;
Glycerol-1,2,3-triarachinate;
Glycerol-1,2,3-trioctanoate;
Glycerol-1,2,3-tripelargonate;
Glycerol-1,2,3-triheptanoate (Fluka);
Mygliol 812 (saturated glycerol-1,2,3-tri-fatty acid ester that is liquid at room temperature and has fatty acids with medium chain length, mainly glycerol-1,2,3-tri-fatty acid esters of caprylic acid and capric acid);

Calcium carbonate (precipitated, conforming to Ph. Eur., Fluka);

β-tricalcium carbonate (in-house synthesis);

Calcium sulfate dihydrate (Fluka, conforming to Ph. Eur., Fluka);

Calcium sulfate hemihydrate (in-house synthesis by thermal dehydration using Fluka calcium sulfate dihydrate);

6-Aminocaproic acid (Fluka);

4-(Aminomethyl)benzoic acid (Aldrich);

trans-4-(Aminomethyl)cyclohexan-1-carbonic acid (tranexamic acid);

Lµtrol® micro 127 (poly(propylene glycol-co-ethylene glycol, Aldrich);

Gentamicin sulfate (activity coefficient 600).

Examples 1-6

Hemostatic agents according to the invention comprising the compositions and properties according to Table 1 below were produced in Examples 1-6.

For this purpose, first, the quantities of glycerol-1,2,3-tripalmitate and glycerol-1,2,3-trioctanoate were weighed into a beaker. Then, the resulting mixtures were heated for 30 minutes to 80° C. while stirring, leading to the generation of a homogeneous melted mass. After the melted mass had cooled to room temperature, Lµtrol® micro 127 and, optionally, gentamicin sulfate were added. The mixtures were homogenized by kneading or triturating until a homogeneous, colorless mass had been generated in each case.

TABLE 1

Compositions and properties of the hemostatic agents according to Examples 1-6.

| Example | Glycerol-1,2,3-tripalmitate | Lµtrol® micro 127 | Glycerol-1,2,3-trioctanoate | Gentamicin sulfate | Assessment |
|---|---|---|---|---|---|
| 1 | 7.0 g | 9.5 g | 7.0 g | — | Kneadable, solid |
| 2 | 3.5 g | 9.5 g | 7.0 g | — | Kneadable, very soft |
| 3 | 3.5 g | 9.5 g | 6.0 g | — | Kneadable, solid |
| 4 | 7.0 g | 9.5 g | 7.0 g | 0.38 g | Kneadable, solid |
| 5 | 3.5 g | 9.5 g | 7.0 g | 0.33 g | Kneadable, very soft |
| 6 | 3.5 g | 9.5 g | 6.0 g | 0.31 g | Kneadable, solid |

Examples 7-24

Hemostatic agents according to the invention comprising the compositions and properties according to Table 2 below were produced in Examples 7-24.

For this purpose, first, the specified quantities of the respective glycerol-1,2,3-tri-fatty acid esters were weighed into a beaker. Then, the resulting mixtures were heated for 30 minutes to 80° C. while stirring, leading to the generation of a homogeneous melted mass. After the melted mass had cooled to room temperature, Lµtrol® micro 127 and, optionally, gentamicin sulfate were added. The mixtures were homogenized by kneading or triturating until a homogeneous, colorless mass had been generated in each case.

TABLE 2

Compositions and properties of the hemostatic agents according to Examples 7-24.

| Example | Glycerol-1,2,3-tri-fatty acid ester | Lutrol® micro 127 | Liquid glycerol-1,2,3-tri-fatty acid ester | Gentamicin sulfate | Assessment |
|---|---|---|---|---|---|
| 7 | 3.5 g glycerol-1,2,3-trimyristate | 9.5 g | 7.0 g glycerol-1,2,3-trioctanoate | — | Kneadable, very soft |
| 8 | 3.5 g glycerol-1,2,3-tristearate | 9.5 g | 7.0 g glycerol-1,2,3-trioctanoate | — | Kneadable, soft |
| 9 | 3.5 g glycerol-1,2,3-triarachinate | 9.5 g | 7.0 g glycerol-1,2,3-trioctanoate | — | Kneadable, soft |
| 10 | 3.5 g glycerol-1,2,3-trimyristate | 9.5 g | 7.0 g Mygliol 812 | — | Kneadable, soft |
| 11 | 3.5 g glycerol-1,2,3-tristearate | 9.5 g | 7.0 g Mygliol 812 | — | Kneadable, soft |
| 12 | 3.5 g glycerol-1,2,3-triarachinate | 9.5 g | 7.0 g Mygliol 812 | — | Kneadable, |
| 13 | 3.5 g glycerol-1,2,3-tripalmitate | 9.5 g | 7.0 g glycerol-1,2,3-triheptanoate | — | Kneadable, soft |
| 14 | 3.5 g glycerol-1,2,3-stearate | 9.5 g | 7.0 g glycerol-1,2,3-triheptanoate | — | Kneadable, very soft |
| 15 | 3.5 g glycerol-1,2,3-tripalmitate | 9.5 g | 7.0 g glycerol-1,2,3-tripelargonate | — | Kneadable, very soft |
| 16 | 3.5 g glycerol-1,2,3-trimyristate | 9.5 g | 7.0 g glycerol-1,2,3-trioctanoate | 0.31 g | Kneadable, very soft |
| 17 | 3.5 g glycerol-1,2,3-tristearate | 9.5 g | 7.0 g glycerol-1,2,3-trioctanoate | 0.31 g | Kneadable, soft |
| 18 | 3.5 g glycerol-1,2,3-triarachinate | 9.5 g | 7.0 g glycerol-1,2,3-trioctanoate | 0.31 g | Kneadable, soft |
| 19 | 3.5 g glycerol-1,2,3-trimyristate | 9.5 g | 7.0 g Mygliol 812 | 0.31 g | Kneadable, very soft |
| 20 | 3.5 g glycerol-1,2,3-tristearate | 9.5 g | 7.0 g Mygliol 812 | 0.31 g | Kneadable, soft |
| 21 | 3.5 g glycerol-1,2,3-triarachinate | 9.5 g | 7.0 g Mygliol 812 | 0.31 g | Kneadable, |
| 22 | 3.5 g glycerol-1,2,3-tripalmitate | 9.5 g | 7.0 g glycerol-1,2,3-triheptanoate | 0.31 g | Kneadable, soft |
| 23 | 3.5 g glycerol-1,2,3-stearate | 9.5 g | 7.0 g glycerol-1,2,3-triheptanoate | 0.31 g | Kneadable, very soft |
| 24 | 3.5 g glycerol-1,2,3-tripalmitate | 9.5 g | 7.0 g glycerol-1,2,3-tripelargonate | 0.31 g | Kneadable, very soft |

Examples 25-58

Hemostatic agents according to the invention comprising the compositions and properties according to Tables 3 to 7 below were produced in Examples 25-58.

For this purpose, first, the quantities of the ingredients specified in Tables 3 to 7 were weighed into a beaker and mixed with each other by stirring. Then, the resulting mixtures were heated to 80° C. for 30 to 60 minutes. After the melted mass had cooled to room temperature, the material was homogenized by kneading or triturating until a homogeneous, colorless mass was produced in each case.

TABLE 3

Compositions and properties of the hemostatic agents according to Examples 25-31.

| Example | Glycerol-1,2,3-tri-fatty acid ester | Calcium carbonate | Liquid glycerol-1,2,3-fatty acid ester | Assessment |
|---|---|---|---|---|
| 25 | 7.0 g glycerol-1,2,3-tristearate | 9.5 g | 7.0 g glycerol-1,2,3-trioctanoate | Wax-like, malleable |
| 26 | 7.0 g glycerol-1,2,3-tristearate | 9.0 g | 7.0 g glycerol-1,2,3-trioctanoate | Wax-like, malleable |
| 27 | 7.0 g glycerol-1,2,3-tristearate | 8.0 g | 7.0 g glycerol-1,2,3-trioctanoate | Wax-like, malleable |

TABLE 3-continued

Compositions and properties of the hemostatic agents according to Examples 25-31.

| Example | Glycerol-1,2,3-tri-fatty acid ester | Calcium carbonate | Liquid glycerol-1,2,3-fatty acid ester | Assessment |
|---|---|---|---|---|
| 28 | 7.0 g glycerol-1,2,3-trimyristate | 9.0 g | 7.0 g glycerol-1,2,3-trioctanoate | Wax-like, malleable |
| 29 | 7.0 g glycerol-1,2,3-tripalmitate | 9.0 g | 7.0 g glycerol-1,2,3-trioctanoate | Wax-like, malleable |
| 30 | 7.0 g glycerol-1,2,3-trisarachinate | 9.0 g | 7.0 g glycerol-1,2,3-trioctanoate | Wax-like, viscous, malleable |
| 28 | 7.0 g glycerol-1,2,3-trimyristate | 9.0 g | 7.0 g Mygliol 812 | Wax-like, malleable |
| 29 | 7.0 g glycerol-1,2,3-tripalmitate | 9.0 g | 7.0 g Mygliol 812 | Wax-like, malleable |
| 30 | 7.0 g glycerol-1,2,3-tristearate | 9.0 g | 7.0 g Mygliol 812 | Wax-like, malleable |
| 31 | 7.0 g glycerol-1,2,3-trisarachinate | 9.0 g | 7.0 g Mygliol 812 | Wax-like, viscous, malleable |

TABLE 4

Compositions and properties of the hemostatic agents according to Examples 32 to 40.

| Example | Glycerol-1,2,3-tri-fatty acid ester | Calcium sulfate hemihydrate | Calcium carbonate | Liquid glycerol-1,2,3-tri-fatty acid ester | Assessment |
|---|---|---|---|---|---|
| 32 | 6.5 g glycerol-1,2,3-tripalmitate | 52.8 | 13.2 g | 27.5 g glycerol-1,2,3-trioctanoate | Malleable without heating |
| 33 | 6.8 g glycerol-1,2,3-tripalmitate | 54.6 g | 13.6 g | 25.0 g glycerol-1,2,3-trioctanoate | Malleable without heating, somewhat more solid than in example 32 |
| 34 | 6.5 g glycerol-1,2,3-trimyristate | 52.8 | 13.2 g | 27.5 g glycerol-1,2,3-trioctanoate | Malleable without heating |
| 35 | 6.5 g glycerol-1,2,3-stearate | 52.8 | 13.2 g | 27.5 g glycerol-1,2,3-trioctanoate | Malleable without heating |
| 36 | 6.5 g 6,5 g glycerol-1,2,3-arachinate | 52.8 | 13.2 g | 27.5 g glycerol-1,2,3-trioctanoate | Malleable without heating |
| 37 | 6.5 g glycerol-1,2,3-tripalmitate | 52.8 | 13.2 g | 27.5 g Mygliol 812 | Malleable without heating |
| 38 | 6.5 g glycerol-1,2,3-trimyristate | 52.8 | 13.2 g | 27.5 g glycerol-1,2,3-trioctanoate | Malleable without heating |
| 39 | 6.5 g glycerol-1,2,3-stearate | 52.8 | 13.2 g | 27.5 g glycerol-1,2,3-trioctanoate | Malleable without heating |
| 40 | 6.5 g 6,5 g glycerol-1,2,3-arachinate | 52.8 | 13.2 g | 27.5 g glycerol-1,2,3-trioctanoate | Malleable without heating |

TABLE 5

Compositions and properties of the hemostatic agents according to Examples 41 and 44.

| Example | Glycerol-1,2,3-tripalmitate | Calcium sulfate dihydrate | Calcium carbonate | Liquid glycerol-1,2,3-tri-fatty acid ester | Gentamicin sulfate | Assessment |
|---|---|---|---|---|---|---|
| 41 | 6.4 g | 51.9 g | 13.0 g | 27.1 g glycerol-1,2,3-trioctanoate | 1.6 g | Malleable without heating |

TABLE 5-continued

Compositions and properties of the hemostatic agents according to Examples 41 and 44.

| Example | Glycerol-1,2,3-tripalmitate | Calcium sulfate dihydrate | Calcium carbonate | Liquid glycerol-1,2,3-tri-fatty acid ester | Gentamicin sulfate | Assessment |
|---|---|---|---|---|---|---|
| 42 | 6.7 g | 53.7 g | 13.4 g | 24.6 g glycerol-1,2,3-trioctanoate | 1.6 g | Malleable without heating |
| 43 | 6.4 g | 51.9 g | 13.0 g | 27.1 g Mygliol 812 | 1.6 g | Malleable without heating |
| 44 | 6.7 g | 53.7 g | 13.4 g | 24.6 g Mygliol 812 | 1.6 g | Malleable without heating |

TABLE 6

Compositions and properties of the hemostatic agents according to Examples 45-50.

| Example | Glycerol-1,2,3-tristearate | β-Tri-calcium sulfate | Calcium carbonate | Glycerol-1,2,3-trioctanoate | ε-Amino-carbonic acid | Assessment |
|---|---|---|---|---|---|---|
| 45 | 7.0 g | 3.5 g | 6.5 g | 7.0 g glycerol-1,2,3-trioctanoate | 0.2 g 6-Amino-caproic acid | Malleable without heating |
| 46 | 7.0 g | 3.5 g | 6.5 g | 7.0 g glycerol-1,2,3-trioctanoate | 0.2 g trans-4-(Aminomethyl)-cyclohexan-1-carbonic acid | Malleable without heating |
| 47 | 7.0 g | — | 9.5 g | 7.0 g glycerol-1,2,3-trioctanoate | 0.2 g 4-(Aminomethyl)benzoic acid | Malleable without heating |
| 48 | 7.0 g | 3.5 g | 6.5 g | 7.0 g Mygliol 812 | 0.2 g 6-Amino-caproic acid | Malleable without heating |
| 49 | 7.0 g | 3.5 g | 6.5 g | 7.0 g Mygliol 812 | 0.2 g trans-4-(Aminomethyl)-cyclohexan-1-carbonic acid | Malleable without heating |
| 50 | 7.0 g | — | 9.5 g | 7.0 g Mygliol 812 | 0.2 g 4-(Aminomethyl)benzoic acid | Malleable without heating |

TABLE 7

Compositions and properties of the hemostatic agents according to Examples 51-58.

| Example | Glycerol-1,2,3-tri-fatty acid ester | Calcium carbonate | Liquid glycerol-1,2,3-tri-fatty acid ester | Calcium chloride | ε-Aminocarbonic acid | Assessment |
|---|---|---|---|---|---|---|
| 51 | 7.0 g glycerol-1,2,3-tristearate | 9.5 g | 7.0 g glycerol-1,2,3-trioctanoate | 0.3 g | 0.2 g 6-Amino-caproic acid | Malleable without heating |
| 52 | 7.0 g glycerol-1,2,3-tristearate | 9.5 g | 7.0 g glycerol-1,2,3-trioctanoate | 0.3 g | 0.2 g trans-4-(Aminomethyl)-cyclohexan-1-carbonic acid | Malleable without heating |
| 53 | 7.0 g glycerol-1,2,3-tristearate | 9.5 g | 7.0 g glycerol-1,2,3-trioctanoate | 0.2 g | 0.2 g 4-(Aminomethyl)benzoic acid | Malleable without heating |

TABLE 7-continued

Compositions and properties of the hemostatic agents according to Examples 51-58.

| Example | Glycerol-1,2,3-tri-fatty acid ester | Calcium carbonate | Liquid glycerol-1,2,3-tri-fatty acid ester | Calcium chloride | ε-Aminocarbonic acid | Assessment |
|---|---|---|---|---|---|---|
| 54 | 7.0 g glycerol-1,2,3-tristearate | 9.5 g | 7.0 g Mygliol 812 | 0.3 g | 0.2 g 6-Amino-caproic acid | Malleable without heating |
| 55 | 7.0 g glycerol-1,2,3-tristearate | 9.5 g | 7.0 g Mygliol 812 | 0.3 g | 0.2 g trans-4-(Aminomethyl)-cyclohexan-1-carbonic acid | Malleable without heating |
| 56 | 7.0 g glycerol-1,2,3-tristearate | 9.5 g | 7.0 g Mygliol 812 | 0.2 g | 0.2 g 4-(Aminomethyl) benzoic acid | Malleable without heating |
| 57 | 7.0 g glycerol-1,2,3-trimyristate | 9.5 g | 7.0 g Mygliol 812 | 0.2 g | 0.2 g 4-(Aminomethyl)benzoic acid | Malleable without heating |
| 58 | 7.0 g glycerol-1,2,3-tripalmitate | 9.5 g | 7.0 g Mygliol 812 | 0.2 g | 0.2 g 4-(Aminomethyl) benzoic acid | Malleable without heating |

A total of 5 g each of the kneadable masses produced in Examples 1-58 were placed in 20 ml deionized water. The pH was tested after 24 hours of storage at room temperature. In all cases, no changes of the pH value as compared to the pH value of deionized water of 6.5 were measured.

Moreover, a Zweymüller hip prosthesis was coated with the mixtures of Examples 1-6 by forming the mixtures into cylinders and subsequently spreading the cylinders over the cylinder surface. The relative motion of the structured surface of the prosthesis with respect to the cylinder caused material to be transferred from the cylinder to the surface of the prosthesis. Depending on the pressure of application and the number of repetitions of the transfer processes, between 80 and 150 mg of the material of the mixtures from Examples 1-6 were transferred.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A malleable, biodegradable hemostatic agent comprising a malleable, biodegradable composition having hemostatic properties, the composition containing a homogeneous mixture of the following components:
   (a) 3% to 50% by weight of at least one saturated glycerol-1,2,3-tri-fatty acid ester having a melting temperature above 37° C.;
   (b) 10% to 80% by weight of at least one filling agent at least partially present in particulate form and having a melting temperature above 37° C., wherein component (b) has a solubility at a temperature of 25° C. of at least 100 grams per liter of water and is selected from the group consisting of polymers of at least one alkylene oxide and copolymers of at least one alkylene oxide; and
   (c) 10% to 50% by weight of at least one compound having a melting temperature not above 37° C. and a solubility at a temperature of 25° C. of less than 50 grams per liter of water, wherein component (c) is a saturated fatty acid ester, wherein all % by weight are relative to a total weight of the hemostatic agent.

2. The malleable, biodegradable hemostatic agent according to claim 1, wherein the hemostatic agent has a pH in water at a temperature of 25° C. in a range of 5.0-9.0.

3. The malleable, biodegradable hemostatic agent according to claim 1, wherein the hemostatic agent has a pH in water at a temperature of 25° C. in a range of 5.5-8.5.

4. The malleable, biodegradable hemostatic agent according to claim 1, wherein component (b) has a solubility at a temperature of 25° C. of less than 50 grams per liter of component (c).

5. The malleable, biodegradable hemostatic agent according to claim 1, wherein component (a) is selected from the group consisting of saturated glycerol-1,2,3-tri-fatty acid esters comprising at least one fatty acid residue of 12-28 carbon atoms.

6. The malleable, biodegradable hemostatic agent according to claim 1, wherein component (a) is selected from the group consisting of saturated glycerol-1,2,3-tri-fatty acid esters comprising at least one fatty acid residue of 14-24 carbon atoms.

7. The malleable, biodegradable hemostatic agent according to claim 1, wherein component (a) is selected from the group consisting of glycerol-1,2,3-tribehenic acid ester, glycerol-1,2,3-tristearic acid ester, and glycerol-1,2,3-tripalmitic acid ester.

8. The malleable, biodegradable hemostatic agent according to claim 1, wherein component (b) is selected from the group consisting of poloxamers, polyethylene glycols, and poly(propylene glycol-co-ethylene glycol).

9. The malleable, biodegradable hemostatic agent according to claim 1, wherein component (c) is selected from the group consisting of (i) esters of polyols and at least one fatty acid, (ii) alkyl fatty acid esters, and (iii) esters of polyethers and fatty acids.

10. The malleable, biodegradable hemostatic agent according to claim 9, wherein component (c) is selected from the group consisting of glycerol-1,2,3-trioctylester, mixed esters of glycerol and caprylic acid and lauric acid, propane-1,2-diol-di-fatty acid esters, and fatty acid esters of 1,3-dihydroxy-2,2-di(hydroxymethyl)propane, lauric acid ethylester, myristic acid methylester, myristic acid ethylester, myristic acid isopropylester, palmitic acid methylester, palmitic acid ethylester, palmitic acid isopropylester, and ethylene glycol fatty acid esters.

11. The malleable biodegradable hemostatic agent according to claim 1, wherein component (c) is not an ester of lauric acid.

12. The malleable, biodegradable hemostatic agent according to claim 1, wherein component (c) is selected from the group consisting of glycerol-1,2,3-trioctylester, esters of glycerol and caprylic acid, propane-1,2-diol-di-fatty acid esters, and fatty acid esters of 1,3-dihydroxy-2,2-di(hydroxymethyl)propane, myristic acid methylester, myristic acid ethylester, myristic acid isopropylester, palmitic acid methylester, palmitic acid ethylester, palmitic acid isopropylester, and ethylene glycol fatty acid esters.

13. The malleable, biodegradable hemostatic agent according to claim 1, further comprising at least one fibrinolysis inhibitor selected from the group consisting of ε-aminocarbonic acids.

14. The malleable, biodegradable hemostatic agent according to claim 1, further comprising at least one substance selected from the group consisting of antibiotics and antiseptic agents.

15. A method for forming a malleable, biodegradable hemostatic agent, the method comprising the steps of:
(a) providing a malleable, biodegradable hemostatic agent according to claim 1;
(b) heating the malleable, biodegradable hemostatic agent to a temperature in a range of 35-40° C.; and
(c) forming the heated malleable, biodegradable hemostatic agent.

16. The method according to claim 15, wherein at least one of the heating and the forming is effected by a hand of a user of the malleable, biodegradable hemostatic agent.

17. A medical implant having a coating comprising the malleable, biodegradable hemostatic agent according to claim 1.

* * * * *